US012042415B2

(12) United States Patent
Salvatelli et al.

(10) Patent No.: US 12,042,415 B2
(45) Date of Patent: Jul. 23, 2024

(54) ORTHOSIS BRACE WITH MONITORING SYSTEM

(71) Applicant: OPTIMA MOLLITER SRL, Civitanova Marche (IT)

(72) Inventors: Susanna Salvatelli, Civitanova Marche (IT); Alberto Salvatelli, Porto Potenza Picena (IT); Franco Salvatelli, Civitanova Marche (IT)

(*) Notice: Subject to any disclaimer, the term of this patent is extended or adjusted under 35 U.S.C. 154(b) by 532 days.

(21) Appl. No.: 17/417,833

(22) PCT Filed: Mar. 13, 2020

(86) PCT No.: PCT/EP2020/056879
§ 371 (c)(1),
(2) Date: Jun. 24, 2021

(87) PCT Pub. No.: WO2020/187753
PCT Pub. Date: Sep. 24, 2020

(65) Prior Publication Data
US 2022/0071791 A1    Mar. 10, 2022

(30) Foreign Application Priority Data
Mar. 20, 2019  (IT) .......................... 102019000004017

(51) Int. Cl.
*A61F 5/01*      (2006.01)
*G01P 1/07*      (2006.01)
(Continued)

(52) U.S. Cl.
CPC ............... *A61F 5/0111* (2013.01); *G01P 1/07* (2013.01); *G01P 15/18* (2013.01); *G16H 40/67* (2018.01)

(58) Field of Classification Search
CPC ..... A61B 5/0022; A61B 5/1036; A61B 5/112; A61B 5/6807; A61F 5/0111;
(Continued)

(56) References Cited

U.S. PATENT DOCUMENTS 10,864,100 B2* 12/2020 Walsh ................... A61F 5/0102
11,389,367 B2*  7/2022 Mooney ................. A61H 3/00
(Continued)

FOREIGN PATENT DOCUMENTS

EP      2204146 A1     7/2010
WO   2016184533 A1    11/2016

OTHER PUBLICATIONS

International Search Report for corresponding PCT/EP2020/056879, dated Jun. 4, 2020.
(Continued)

*Primary Examiner* — Andre J Allen
(74) *Attorney, Agent, or Firm* — Egbert, McDaniel & Swartz, PLLC

(57) ABSTRACT

An orthosis brace includes: a brace suitable for being worn on a patient's foot; a dedicated electronic device applied on the brace; a software platform on the Internet; a smart device held by the patient and provided with an app to access the software platform; and a smart device held by the therapist and provided with an app to access the software platform. The dedicated electronic device has a motion sensor array composed of an IMU suitable for detecting the motion of the brace, a control unit suitable for processing the data from said IMU to detect a removal of the brace, and a wireless telecommunication module suitable for sending the data processed by the dedicated electronic device to the software platform.

13 Claims, 3 Drawing Sheets

(51) Int. Cl.
*G01P 15/18* (2013.01)
*G16H 40/67* (2018.01)

(58) Field of Classification Search
CPC . A61F 5/0127; A43B 3/34; G01P 1/07; G01P 15/18; G16H 40/67
See application file for complete search history.

(56) References Cited

U.S. PATENT DOCUMENTS

| | | | |
|---|---|---|---|
| 11,419,748 B2* | 8/2022 | Zelen | A61F 5/0195 |
| 2013/0217998 A1* | 8/2013 | Mahfouz | A61B 5/1114 |
| | | | 600/595 |
| 2017/0296115 A1 | 10/2017 | Mahfouz et al. | |
| 2017/0319368 A1 | 11/2017 | Selner | |
| 2017/0360586 A1 | 12/2017 | Dempers et al. | |
| 2019/0021894 A1 | 1/2019 | Zelen et al. | |
| 2021/0338469 A1* | 11/2021 | Dempers | A61F 5/0123 |
| 2021/0393427 A1* | 12/2021 | Mirza | A61B 5/6812 |
| 2022/0008237 A1* | 1/2022 | Mirza | G06N 20/00 |
| 2022/0409098 A1* | 12/2022 | Mcdaid | A61H 1/024 |
| 2023/0372186 A1* | 11/2023 | Rovekamp, Jr. | A61F 5/05858 |
| 2024/0000649 A1* | 1/2024 | Spenciner | A61N 1/0452 |

OTHER PUBLICATIONS

Written Opinion of the International Searching Authority for corresponding PCT/EP2020/056879, dated Jun. 4, 2020.
Bae et al., "A tele-monitoring system for gait rehabilitation with an inertial measurement unit and a shoe-type ground reaction force sensor", MECHATRONICS, vol. 23, No. 6, Sep. 1, 2013, pp. 646-651.

\* cited by examiner

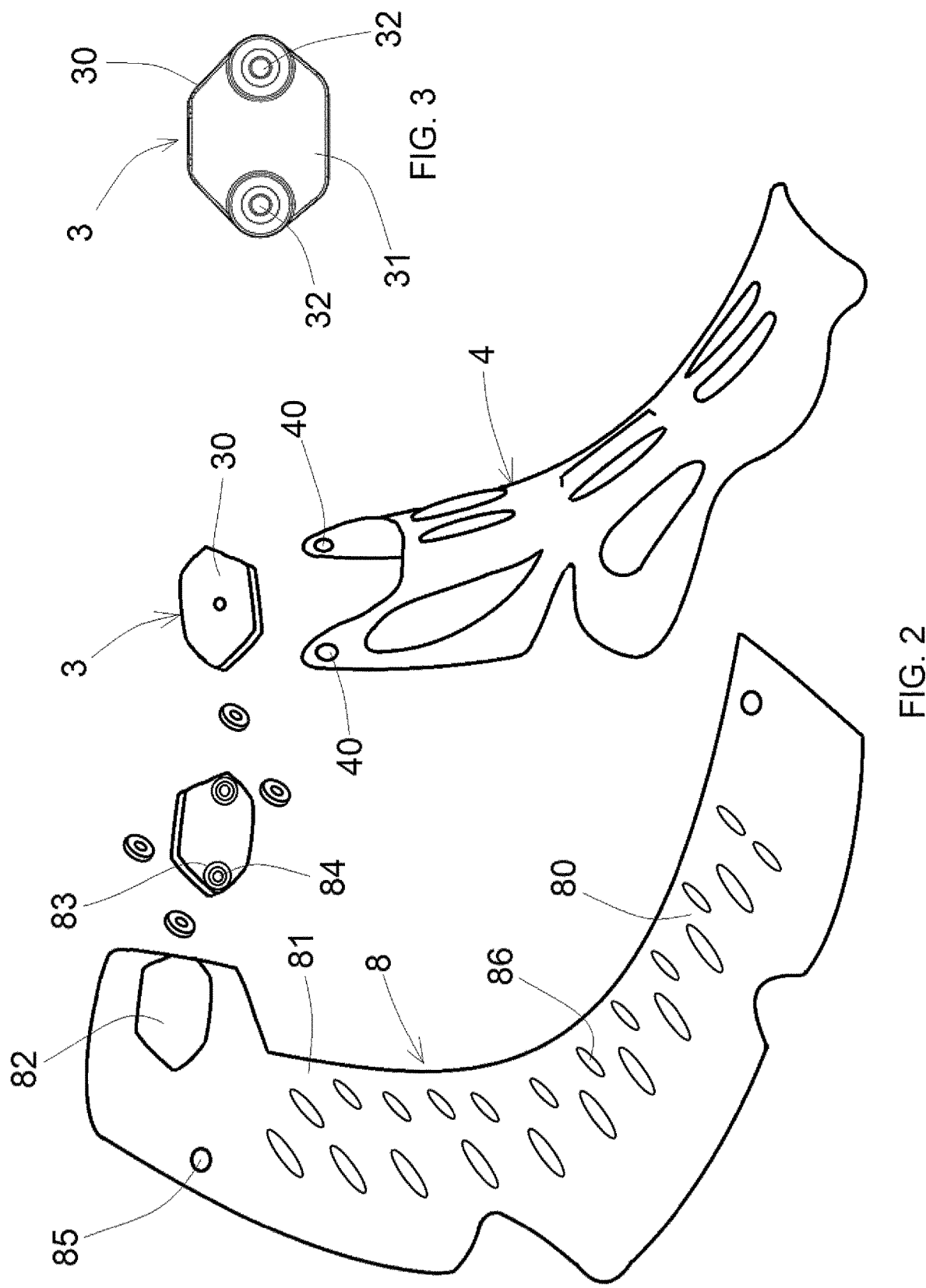

ORTHOSIS BRACE WITH MONITORING SYSTEM

The present invention relates to an orthosis brace, in particular for diabetic foot, provided with a system used to monitor the motion, the stand-by and the removal of the brace.

Diabetic patients are often elder, obese patients affected by co-morbidity and generally self-managed. When they are affected by peripheral neuropathy (lack of pain perception in the peripheries of the body: hands and feet), patients are unable to comply with the rehabilitation therapies of the chronic acute foot injury, and are often unaware of the risk of degenerative amputation.

The use of rehabilitative walking devices, such as orthosis braces, which immobilize the foot in a correct position, discharging the weight on the ulcered/injured part of the foot, is a life-saving measure for this type of patients.

The fact that the patient can remove said device during the acute stage of the injury (for a lack of pain perception and/or for the incorrect conviction that the injury can be managed wearing ordinary shoes or walking barefoot) exposes the patient to a number of risks that frustrate the work of the therapist, who is unable to control said risks.

Said risks are not limited to degeneration of the infected injury, gangrene and amputation, and can severely impair the life expectancy of the patient. As it is known, the life expectancy of a diabetic patient who has suffered the amputation of foot, thigh or leg is generally lower than 5 years after amputation because of additional major problems and pathologies.

EP2204146 and WO2016184533, in the name of the same applicant, disclose a footwear orthosis and a foot brace, in particular for diabetic foot.

However, in addition to the technical and functional quality of these brace technologies, the compliance (adherence to treatment) of the patient in wearing the brace is fundamental for the success of the therapy. For this reason, these types of braces are generally provided with an anti-removal system, such as plastic straps that are closed and sealed to guarantee the use of the brace. Such an anti-removal system is closed when the brace is worn and is opened by the doctor at the end of the therapy.

However, the aforesaid anti-removal system is considered as a coercive measure by the patient and for this reason it is not easily tolerated. In fact, such an anti-removal system is opposed by the patients, who eventually refuse the therapy. Moreover, in case of an infected ulcer, the anti-removal system cannot be used because of the frequent medications that must be performed several times a week.

US2019021894 discloses an orthopedic brace that comprises a controller disposed in a body of the brace in a lateral external portion of the ankle. The controller comprises motion sensors (accelerometers and/or gyroscopes) suitable for detecting the motion of the brace and for sending data to a central device and a smart device held by the therapist in such a way the therapist can analyze whether the patient is using the brace correctly. US2019021894 does not disclose or discuss the technical problem represented by the fact that the patient may remove the brace. The motion sensors are not an inertial measurement unit (IMU) capable of providing 9-axes data. The controller has no firmware capable of processing the sensor data to detect the removal of the brace.

The purpose of the present invention is to eliminate the drawbacks of the prior art by disclosing an orthosis brace with monitoring system that avoids the use of the anti-removal system and provides the therapist with information on the use and on the removal of the brace.

Another purpose of the present invention is to disclose such an orthosis brace with monitoring system that induces the patient to use the brace correctly.

These purposes are achieved according to the invention with the characteristics of the independent claim 1.

Advantageous embodiments of the invention appear from the dependent claims.

Projects, studies, investigations and tests performed by the applicant have shown that, if a brace is provided with invisible sensors (which are in any case effective and efficacious for controlling, monitoring and data collecting purposes), the patient does not refuse the use of the brace and does not feel controlled or forced by the therapist, although these actions are performed by the sensors in a timely, effective and efficacious way.

Hence the intuition consists in replacing the anti-removal system, which is visibly coercive and sometimes claustrophobic, with a monitoring system with sensors that has proved to be a valid, effective, invisible alternative solution that is well tolerated by the patients.

The orthosis brace according to the invention is defined by claim 1.

Additional features of the invention will be clearer from the following detailed description, which refers to a merely illustrative, not limiting embodiment, as shown in the appended figures, wherein:

FIG. 2 is an exploded perspective view of some parts of the orthosis brace according to FIG. 1;

FIG. 3 is a back view of a box that contains a dedicated electronic device of the orthosis brace according to the invention;

Figure 1:
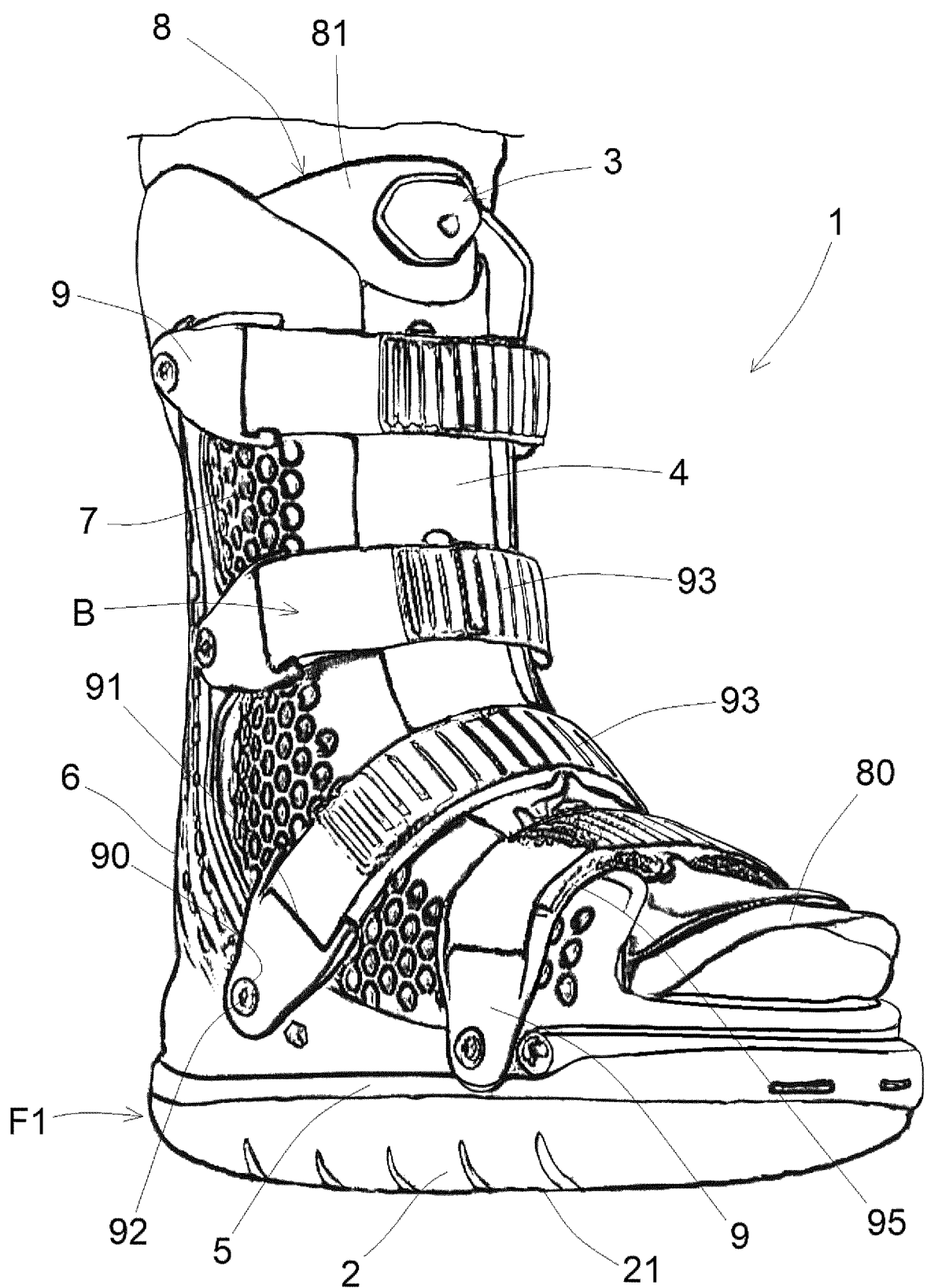
FIG. 1 is a perspective view of the orthosis brace according to the invention.

The brace (1) comprises a bottom (F1) comprising a sole (2) made of a soft material and a stiffening plate (5) associated with the sole (2) and fixed onto the sole (2).

The sole (2) comprises a tread (21) intended to come in contact with the ground. The sole (2) is obtained by molding a soft thermoformable plastic material such as, for instance, soft thermoplastic polyurethane or soft EVA.

The stiffening plate (5) of the brace is rigid and non-deformable and is made of a rigid material, preferably rigid polyurethane.

The stiffening plate (5) is glued to the sole (2) in order to increase the hardness and the rigidity of the surface whereon the patient's foot rests and in order to avoid flexing the sole (2) longitudinally during ambulation.

The brace (1) comprises a body (6) made of a rigid plastic material, preferably rigid propylene. The body (6) is connected to the stiffening plate (5) in fit-in coupling mode. The body (6) is longitudinally provided with an L-shaped configuration and is disposed in a back portion of the brace, in such a way to be positioned behind the heel and behind the back portion of the patient's tibia.

The brace (1) comprises a monolithic upper (7) that is obtained by molding a soft, washable, thermoformable material, advantageously EVA. The upper (7) has a net or grid structure with a plurality of through holes.

The upper (7) comprises a back portion and two lateral portions. The back portion (70) of the upper is curved in cross-section and has a concavity intended to be faced towards the patient's Achilles tendon, in such a way to surround the patient's calcaneus and the back part of the tibia. In particular, the back portion of the upper has a concavity that corresponds to the concavity of the back portion of the body. The lateral portions of the upper frontally extend from the back portion in such a way to surround the internal side and the external side of the foot of the patient who is wearing the brace. The upper (7) is connected to the body (6) in fit-in coupling mode.

The brace (1) is also provided with a tibial protection (8) provided with L-shaped configuration in cross-section. The tibial protection (8) comprises a horizontal portion (80) suitable for surrounding the back of the patient's foot, and a vertical portion (81) suitable for surrounding the patient's tibia.

The horizontal portion (80) and the vertical portion (81) of the tibial protection have a curved shape in cross-section and a concavity suitable for being directed towards the back of the patient's foot and towards the patient's tibia.

The tibial protection (8) is made of the same material used for the upper (7); in particular, the tibial protection (8) is a monolithic piece preferably made of EVA, with a net or grid structure and a plurality of holes (86) that can be through holes or blind holes.

With reference to FIG. 2, a recessed seat (82) is obtained in an upper portion of the tibial protection (8). The recessed seat (82) of the tibial protection receives a flange (83) composed of a conductive metal plate, for example made of brass. The flange (83) is provided with two female seats (84).

Figure 4:
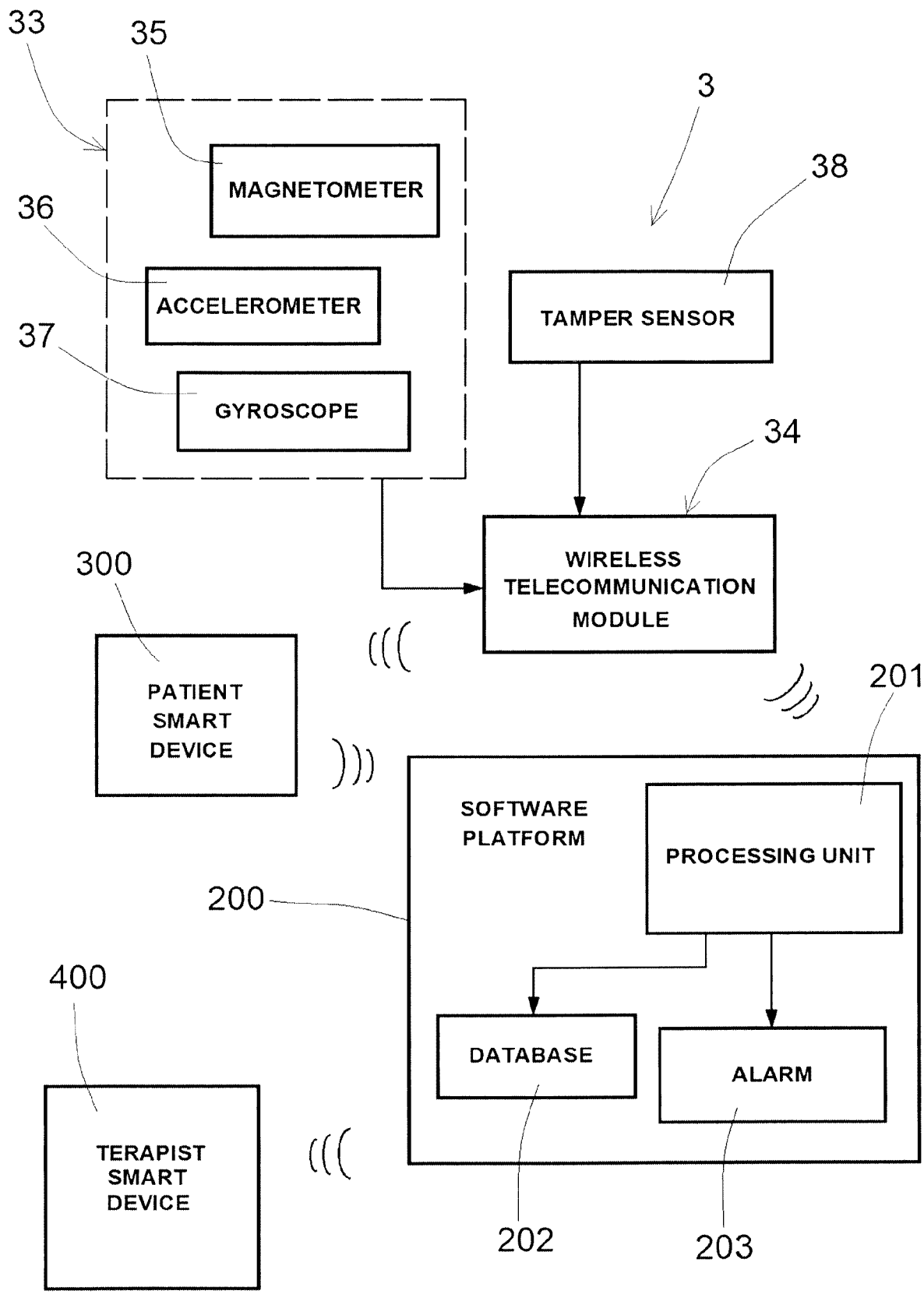
FIG. 4 is a block diagram that shows the operation of the orthosis brace according to the invention; and With reference to the Figures, the orthosis brace of the invention is disclosed, which is generally indicated with reference numeral (1).

A dedicated electronic device (3) is disposed in a box (30) that is removably fixed to the flange (83). The box (83) has a back surface (31) provided with two male clips (32) (FIG. 3) that are coupled in the female seats (84) of the flange in fit-in coupling mode. The two male clips (32) of the box operate as terminals of a normally open switch (SW) (FIG. 4). When the male clips (32) of the box are coupled with the female seats (84) of the flange, the electric conductivity of the flange (83) closes the switch (SW) and the dedicated electronic device (3) starts to operate.

A rigid cover (4) that basically has the same shape as the tibial protection is disposed on the tibial protection (8). The rigid cover (4) is provided with hinging holes (40) disposed in upper position along a horizontal axis in such a way to hinge the rigid cover to the tibial protection that is provided with hinging holes (85) in upper position.

The brace (1) comprises fastening means (B) to close the brace and fasten the tibial protection (8) and the rigid cover (4) inside the upper (7). Said fastening means (B) comprise wings (9) that are hinged to the body (6) and straps (93) connected to the wings (9) and closed by means of a tear-off system (95), such as Velcro, or snap buttons.

The wings (9) have a through hole (90) and a slot (91). Each wing (9) is revolvingly connected to the body (6) by means of screws (92) that are inserted in the through hole (90) of the wing (9) and are screwed in the body (6). The straps (93) are slidingly inserted in the slots (91) of the wings to compress the upper (7) and hold the rigid cover (4) and the tibial protection (8).

With reference to FIG. 4, the dedicated electronic device (3) comprises a motion sensor array (33), a control unit (39) and a wireless telecommunication module (34).

The motion sensor array (33) is composed of an inertial measurement unit (IMU) with 9 axes comprising a magnetometer (35), an accelerometer (36) and a gyroscope (37). The IMU is suitably configured to detect a 9-axes motion in the three-dimensional space of the dedicated electronic device (3) fixed to the brace (1).

The control unit (39) is connected to the IMU of the motion sensor array (33) to receive data and process the received data. The control unit (39) comprises a memory (39a) and a processing unit (39b) comprising a firmware wherein a software is installed to implement an algorithm for the recognition of the removal of the brace.

In particular, the control unit (39) of the dedicated electronic device (3) is suitably configured to execute a fast Fourier transform (FFT) of the signals from the IMU of the motion sensor array and compare said fast Fourier transform (FFT) with preset threshold values in order to detect a removal of the brace from the patient's foot.

The wireless telecommunication module (34) is connected to the control unit (39) and is suitable for remotely sending the data processed by the control unit to a software platform (200) on the Internet.

The software platform (200) can be accessed by smart devices (300) of the patient and smart devices (400) of the therapist, which are provided with specifics apps.

The control unit (39) is connected to the switch (SW).

Optionally, the brace (1) can comprise a tamper sensor (38) suitable for detecting the tampering or removal of the dedicated electronic device (3). The tamper sensor (38) can be a switch that detects when the box (30) of the dedicated electronic device is detached from the flange (83) fixed to the tibial protection (8).

Optionally, the brace (1) can comprise at least one pressure sensor (P) disposed in the brace in such a way to detect a pressure exerted by the patient's foot. The pressure sensor (P) is operatively connected to the control unit (39). The control unit (39) is suitably configured in such a way to compare the pressure detected by the pressure sensors with threshold values in order to detect a removal of the brace from the patient's foot.

The wireless telecommunication module (34) can be a Bluetooth module or the like, suitable for connecting to the smart device (300) of the patient or to a router connected to the Internet in order to send the data processed by the control unit to the software platform (200).

The dedicated electronic device (3) can be recharged by means of a power supply unit suitable for being connected to the electric mains. The power supply unit is provided with an USB cable that is connected to the dedicated electronic device (3) or to a wireless charging system.

The software platform (200) has a processing unit (201) suitable for receiving and processing the data sent by the dedicated electronic device (3). The software platform (200) also comprises a database (202), which can be for instance a cloud wherein the data processed by the processing unit (201) is stored, and an alarm (203) configured in such a way to generate an alarm signal to the smart device (400) of the therapist based on the data received from the dedicated electronic device that detects an incorrect use of the brace (1).

The control unit (39) is configured in such a way to send an alarm signal and activate the alarm (203) in the following cases:

A) when it receives a signal from the tamper sensor (38) that indicates that the dedicated electronic device (3) has been removed;

B) when the motion sensors (33) detect that the dedicated electronic device (3) has remained totally motionless for a time higher than a preset threshold time;

C) when the motion sensors (33) detect an abrupt motion of the dedicated electronic device (3) that indicates that the fastening means (B) of the brace have been opened by the patient.

Moreover, based on the data from the motion sensor array (33), the processing unit (201) calculates the patient's ambulation time and mode, measuring and controlling the compliance with the therapy of such ambulation time and mode, in such a way that the therapist can be informed about the patient's rehabilitation.

By means of the smart device (400), the therapist can easily check the patient's compliance data from remote by simply accessing the software platform (200) by means of a browser.

After accessing the software platform (200), the therapist can rapidly consult the data about the compliance of all his/her patients with an aggregated analysis system; likewise, the therapist can make a detailed analysis by entering the data of a specific patient.

The patient is monitored 24 hours per day by means of the dedicated electronic device (3) that sends the data detected by the sensors in Bluetooth mode to the smart device (300) held by the patient with 30-minute time intervals. The patient's smart device (300) sends the data to the software platform (200), which stores the data in the database (202) in the Cloud. In view of the above, by means of the smart device (400), the therapist can interrogate the software platform (200) several times a day and contact the patient promptly if the patient has removed the brace or the dedicated electronic device.

Moreover, the orthosis brace according to the invention has been devised in order to directly affect on the patient's compliance. A sort of patient-therapy interaction has been studied in order to induce a voluntary stimulation in the patient to keep a certain behavior, involving the patient in a sort of interactive game.

The software platform (200) communicates with a dedicated app that is installed on the patient's smart device (300) and can interact with the patient.

The software platform (200) will compare the data transmitted by the dedicated electronic device (3) with a set of expected data (based on algorithms predefined with the doctors and based on typical ambulation time and mode according to the type of patient, the conditions of the disease, the type, extension and position of the injury, the weight of the patient, the age range, etc.) and will interact with the patient in real time by means of the app installed on the patient's smart device, sending messages to encourage or discourage a specific activity.

While the motion sensors and the tamper sensors (33, 38) detect the use or the removal of the brace, the wireless telecommunication module (34) communicates with the software platform (200) that will send instructions to the app in order to interact with the patient with a specific messaging system. Such an encouraging/discouraging operation will be performed using a mechanism that is typical of interactive games, which has been specifically studied to obtain the maximum psychological involvement of the patient, who will not perceive any aspect related with his/her pathology or with the fact that his/her behavior is being controlled by third parties.

A mechanism for an interactive game will be specifically studied in order to stimulate the patient's desire to become an active participant and to be responsible for achieving the goal of the game. The patient will be satisfied when his/her behaviors are displayed as a score (or when a virtual task has been completed) on the smart device. Additionally, the patient will never perceive the control or conditioning action that is exerted by the dedicated electronic device (3) in order to discourage any behavior that does not comply with the therapy.

When the patient is included in the rehabilitation therapy program with the orthosis brace according to the invention, the therapist will access the software platform (200) by means of the smart device (400) or personal computer, configuring the patient's data sheet and including the therapeutic data that will be processed through a system of adherence and monitoring algorithms that will provide pre-configured instructions for the app.

If the patient decides to participate in the therapy and starts wearing the brace (1), the medical center provided with the software platform (200) will enable the patient to download the app in the patient's smart device (300) for connecting to the software platform (200).

Upon the first application of the brace (1), when the fastening means (B) are closed, the system for connecting the brace (1) with the patient's smart device (300) will be activated. The app of the patient's smart device (300) will manage an interactive game that consists in achieving a preset virtual goal (an X score or the completion of a task). In the system schemes, the preset virtual goal will coincide with the completion of a set of correct actions according to the pre-configured instructions (such as for instance the non-removal of the brace, the ambulation for a given period of time per day for a certain number of days, etc.) detected by the dedicated electronic device (3) of the brace and directly analyzed by the software platform (200).

The (motor) actions detected by the motion sensor array (33) will be informed by means of the wireless telecommunication module (34) to the app of the patient's smart device (300), which will analyze the data based on system algorithm and will compare the data with pre-configured instructions from the software platform (200) for the specific patient, performing three types of actions:

1) it will send encouraging or discouraging messages for the specific behavior to the patient: the detection of a correct behavior will correspond to an increase in the score (or in the completion of the task), which will be immediately displayed in the screen of the smart device. Vice versa, the opposite situation will occur in case of detection of an incorrect behavior;
2) it will send the data received from the wireless telecommunication module (34) over the Wi-Fi to the Cloud of the software platform (200). The data will be stored as patient's history and will be made available for consultation to the therapist;
3) if the patient continues on performing actions that are not compliant with the pre-configured instructions for a period of time that is longer than 3 hours, it will send an alert to the software platform by means of the alarm (203) sent to the therapist in such a way that the therapist can promptly and directly contact the patient.

Additionally, the collected data that is stored in the database (202) can be consulted by the therapists in order to assess the therapeutic progress and the interaction of the patient's behavior with the evolution of the rehabilitation or of the criticalities and amputative degenerations.

The operation of the dedicated electronic device (3) is described below.

In a first step, the inputs of the control unit (39) from the motion sensor array (33), from the switch (SW) and from the pressure sensors (P) are considered.

In a second step, the data from the motion sensor array (33) is filtered.

In a third step, a first subroutine is performed to check whether the dedicated electronic device (3) is attached to the brace. In such a subroutine, the analogue data from the switch (SW) is compared with threshold values to detect whether the dedicated electronic device (3) is attached to the flange (83) of the brace.

A decision step is performed according to the result of the first subroutine.

If the dedicated electronic device (3) is not attached to the brace, a warning signal (505) is generated to indicate that the dedicated electronic device (3) is detached. Such a warning signal is sent to the software platform (200) to inform the therapist's smart device (400) and the patient's smart device (300) that the dedicated electronic device (3) is detached from the brace.

If the dedicated electronic device (3) is attached to the brace, a second subroutine is performed to detect the current activity of the patient who is wearing the brace.

The control unit (39) is configured in such a way to detect four possible activities:
  walking, wherein the patient is walking while wearing the brace,
  removing brace, wherein the brace is removed by the patient,
  falling, wherein the patient has fallen into the ground, and
  sitting, wherein the patient is sitting while wearing the brace.

These activities are detected by comparing the data from the IMU of the motion sensor array with preset threshold values.

If one of these possible activities is true, the control unit (39) will store the state of the activity in the memory (39a) and will send information on the activity to the software platform (200).

In particular, if the removal of the brace is true, the control unit (33) will send an alarm signal to the software platform (200) in such a way to inform the therapist's smart device (400) of the removal of the brace.

Optionally, if the walking activity is detected, the control unit (39) will perform a third subroutine to count the patient's steps. The step counting subroutine can be performed according to the signals from the IMU of the motion sensor array. In fact, if the signals are a pulse train, it can be recognized that the patient is walking and each pulse is a step.

The invention claimed is:

1. Orthosis brace comprising:
  a brace suitable for being worn on a patient's foot;
  a dedicated electronic device applied on said brace;
  a software platform on the Internet;
  a smart device held by the patient and provided with an app to access the software platform; and
  a smart device held by a therapist and provided with an app to access the software platform;
  wherein said dedicated electronic device comprises:
    a motion sensor array suitable for detecting the motion of said brace; and
    a wireless telecommunication module suitable for transmitting data to said software platform;
  characterized in that
  said motion sensor array is composed of an inertial measurement unit (IMU) with 9 axes comprising a magnetometer, an accelerometer and a gyroscope and configured to detect a 9-axes motion in the three-dimensional space of the dedicated electronic device; and
  said dedicated electronic device comprises a control unit that is suitably configured to
    receive data from said motion sensor array;
    process said data to detect a removal of the brace from the patient's foot;
    send an alarm signal to the software platform by means of the wireless telecommunication module when a removal of the brace from the patient's foot is detected.

2. The orthosis brace of claim 1, wherein said control unit of the dedicated electronic device is suitably configured to execute a fast Fourier transform (FFT) of the signals from said IMU of the motion sensor array and compare said fast Fourier transform (FFT) with preset threshold values to detect a removal of the brace from the patient's foot.

3. The orthosis brace of claim 1, wherein said dedicated electronic device is disposed in a box fixed to an upper portion of a tibial protection of the brace.

4. The orthosis brace of claim 3, wherein said box of the dedicated electronic device is removably mounted on a flange applied on the upper part of said tibial protection of the brace.

5. The orthosis brace of claim 4, wherein said box comprises two male clips suitable for being coupled in female seats of the flange in fit-in coupling mode; said flange being of a conductive material;
  the two male clips of the box operating as terminals for a normally open switch (SW) that is closed when the two male clips of the box are coupled in the female seats of the flange;
  said switch (SW) being connected to said control unit, and
  said control unit being configured in such a way to send an alarm signal to the software platform by means of the wireless telecommunication module when it detects that the dedicated electronic device is detached from the flange of the brace.

6. The orthosis brace of claim 1, further comprising a tamper sensor suitable for detecting a removal of the dedicated electronic device from the brace.

7. The orthosis brace of claim 1, wherein said wireless telecommunication module comprises a Bluetooth module that is coupled with the smart device of the patient in order to send the data detected by the motion sensor array to said software platform.

8. The orthosis brace of claim 1, wherein said software platform comprises:
  a processing unit suitable for receiving and processing the data sent by said dedicated electronic device;
  a database wherein the data processed by the processing unit is stored; and
  an alarm configured in such a way to generate an alarm signal to the smart device of the therapist when the processing unit detects an incorrect use of the brace based on the received data.

9. The orthosis brace of claim 8, wherein the processing unit is configured in such a way to activate the alarm when the motion sensors detect that the dedicated electronic device has remained completely motionless for a time higher than a preset threshold time.

10. The orthosis brace of claim 8, wherein the processing unit is configured in such a way to activate the alarm when the motion sensors detect an abrupt motion of the dedicated electronic device that indicates that the fastening means of the brace have been opened.

11. The orthosis brace of claim 8, further comprising a tamper sensor suitable for detecting a removal of the dedicated electronic device from the brace, wherein the processing unit is configured in such a way to activate the alarm when it receives a signal from the tamper sensor that indicates that the dedicated electronic device has been removed.

12. The orthosis brace of claim 1, wherein said control unit of the dedicated electronic device is suitably configured to receive data from said IMU of the motion sensor array and detect four possible activities:

walking, wherein the patient is walking while wearing the brace, removing brace, wherein the brace is removed by the patient, falling, wherein the patient has fallen into the ground, and sitting, wherein the patient is sitting while wearing the brace.

13. The orthosis brace of claim 1, at least comprising a pressure sensor disposed in the brace in such a way to detect a pressure exerted by the patient's foot;

said pressure sensor being operatively connected to the control unit that is configured in such a way to compare the pressure detected by the pressure sensors with threshold values in order to detect a removal of the brace from the patient's foot.

\* \* \* \* \*